United States Patent
Gelfand (10) Patent No.: US 8,439,918 B2
(45) Date of Patent: May 14, 2013

(54) ULNA FIXATION

(75) Inventor: Jeffrey Gelfand, Severna Park, MD (US)

(73) Assignee: Suspension Orthopaedic Solutions, Inc., Arnold, MD (US)

( * ) Notice: Subject to any disclaimer, the term of this patent is extended or adjusted under 35 U.S.C. 154(b) by 589 days.

(21) Appl. No.: 12/591,799

(22) Filed: Dec. 1, 2009

(65) Prior Publication Data
US 2010/0137866 A1 Jun. 3, 2010

Related U.S. Application Data

(60) Provisional application No. 61/200,630, filed on Dec. 2, 2008.

(51) Int. Cl.
*A61B 17/56* (2006.01)
*A61B 17/58* (2006.01)
*A61B 17/82* (2006.01)
*A61F 2/30* (2006.01)

(52) U.S. Cl.
USPC .............. 606/74; 606/70; 606/282; 606/286; 606/291

(58) Field of Classification Search ............ 606/280, 606/282, 291, 74
See application file for complete search history.

(56) References Cited

U.S. PATENT DOCUMENTS

| 5,741,259 A * | 4/1998 | Chan ............................. 606/74 |
| 2005/0085818 A1* | 4/2005 | Huebner ......................... 606/69 |

* cited by examiner

*Primary Examiner* — Andrew Yang
(74) *Attorney, Agent, or Firm* — Womble Carlyle Sandridge & Rice, LLP (57) ABSTRACT

An improved means for fixation of a fractured coronoid process of the proximal ulna. A substantially rigid plate is secured to the anterior aspect of the proximal ulna relative to a fracture of the coronoid process of the ulna. The plate contains a hook feature at the proximal aspect and is positioned so that it extends over the proximal/anterior aspect of the coronoid process relative to the fracture. The plate has surfaces that define a plurality of openings through which suture and/or screws can pass. The openings may contain a recess at a side of the plate opposite the ulna. At least one hole is formed in the ulna. At least one anchor may be secured to a flexible device, positioned at a side of the plate opposite the ulna, secured to another anchor on the posterior aspect of the ulna and the flexible device tensioned. At least one screw may be inserted through the plate and into the coronoid process or a bone fragment securing it to the plate.

48 Claims, 7 Drawing Sheets

ULNA FIXATION

CROSS-REFERENCE TO RELATED APPLICATIONS

The present application derives priority from U.S. provisional application No. 61/200,630, filed Dec. 2, 2008.

BACKGROUND OF THE INVENTION

1. Field of the invention

The present invention relates broadly to surgical devices and methods for the internal fixation of fractured bones, and more particularly, to a system and method for fixation of a fractured coronoid process of the proximal ulna.

2. Description of the Background

Coronoid fractures of the proximal ulna may be associated with elbow instability. In certain cases surgical management of coronoid fractures may be indicated. The coronoid process of the ulna can be fractured when the human elbow experiences significant trauma. If there is associated ligamentous injury about the elbow, the joint will often become unstable and result in dislocation or subluxation. In this situation surgical fixation of coronoid fractures is necessary to stabilize the elbow. Because of the small fragment size of the coronoid and its location deep to the soft tissues in the anterior aspect of the elbow, standard methods of fracture fixation are challenging.

SUMMARY OF THE INVENTION

An object of the invention is to provide a bone plate specifically contoured to fit the anterior surface of the proximal ulna for use in the rigid fixation of a coronoid fracture.

In one embodiment, a substantially rigid bone plate for internal fixation of the coronoid process of the proximal ulna comprises a contoured plate having an upper surface and a lower surface that is specifically contoured to fit the anterior surface of the proximal ulna. The proximal aspect of the plate possesses hooked features to capture the most proximal/anterior aspect of the coronoid process. The hooked feature will have reciprocal mating surfaces to the coronoid surface that it is intended to engage. The hooks will apply a force in opposition to any potential displacing forces. A plurality of elongated holes are arranged along the length of the plate to accommodate bone screws, sutures, cables, or other flexible device for securing the plate to the bone. These holes may be round or they may be elongated depending on the particular surgical implementation. These openings may define a recess at a side of the plate opposite the ulna. The recess is adapted to receive an anchor, such as a washer, button, or other securing device. A plurality of threaded holes are arranged along the width of the proximal aspect of the plate to accommodate bone screws for securing the plate to a coronoid fragment or a bone graft. A plurality of smaller holes are also arranged along the width of the proximal aspect of the plate to accommodate suture, cable or other flexible device for fixation of the anterior elbow capsule.

In another embodiment the holes arranged along the length of the plate to accommodate bone screws, sutures, cables, or other flexible devices for securing the plate to the bone are round.

In another embodiment the holes arranged along the length of the plate to accommodate suture, cable or other flexible device for securing the plate to the bone are round and threaded to accommodate bone screws.

In yet another embodiment, the holes arranged along the length of the plate to accommodate suture, cable or other flexible device for securing the plate to the bone, whether elongated or round, may contain a recess or lip around the perimeter of the hole or slot at the side of the plate opposite the ulna. The recess is adapted to receive an anchoring device such as a washer, button or other suitable anchor. When the anchor is manipulated and positioned in the recessed hole, the top surface of the anchor may or may not be flush with the side of the plate opposite the ulna. In some implementations, the anchor can slide in a longitudinal direction within the recess.

In another embodiment, the bone plate may flare out medially as it approaches the hooked features at the proximal extent of the bone plate to follow the natural contours of the proximal ulna and coronoid process.

In another embodiment, the bone plate may flare out laterally as it approaches the hooked features at the proximal extent of the bone plate to follow the natural contours of the proximal ulna and coronoid process.

In still another embodiment, the bone plate may flare out both medially and laterally as it approaches the hooked features at the proximal extent of the bone plate to follow the natural contours of the proximal ulna and coronoid process.

Another objective of the invention is to provide a method of ulna fixation for treatment of a fractured coronoid process of the proximal ulna.

In one embodiment, a method of ulna fixation for treatment of a fractured coronoid process of the proximal ulna comprises, securing a substantially rigid plate with hooked features on its proximal aspect to the anterior aspect of the proximal ulna so that it extends proximally to capture the proximal/anterior aspect of the coronoid process of the proximal ulna in the hooked features. Once the plate is in position on the anterior aspect of the proximal ulna, a low-profile targeting guide is aligned with at least one of the holes arranged along the length of the plate and a bone drill is utilized to form at least one hole through the ulna connecting the posterior and anterior surfaces of the proximal ulna. A suture, cable or other flexible device is secured to an anchor, such as a washer, button or other suitable device. The anchor with the flexible device attached is passed through a hole in the ulna and an opening in the bone plate from posterior to anterior. The anchor is then manipulated into a position wherein it resists passing back through the plate and rests on the anterior surface of the plate. A second anchor is positioned on the posterior of the ulna in proximity to the hole through the ulna. The second anchor is secured to the flexible device that is secured to the first anchor. The flexible device is tensioned securing the second anchor to the posterior aspect of the ulna, thereby securing the plate to the anterior aspect of the proximal ulna. In some implementations, the method of securing the flexible device may be a method of knotless fixation.

In another embodiment, a low-profile targeting guide and bone drill are utilized to place a second hole through the ulna connecting the posterior and anterior surfaces of the proximal ulna and the above process is repeated to provide a more secure application of the plate to the bone.

In another embodiment, a low-profile targeting guide is aligned with at least one of the holes arranged along the length of the plate and a bone screw is inserted through the ulna from posterior to anterior until the tip of the screw captures the threads in the hole in the plate, a threaded washer, or another appropriate capturing device. In some implementations, the holes may not be threaded and a threaded device may be utilized on the side of the plate opposite the ulna to capture the tip of the screw.

In another embodiment, where there is significant compromise of the coronoid process, the coronoid fragment(s) is/are surgically retrieved. The coronoid fragment(s) is/are aligned with the proximal aspect of the plate so as to be adjacent to the threaded holes along the proximal aspect of the plate. Screws are inserted into the threaded holes along the proximal aspect of the bone plate and into the coronoid fragment(s) to secure the coronoid fragment(s) to the bone plate. The screws utilized may be locking or non-locking, self tapping or require that a hole be drilled and tapped. The bone plate with the coronoid fragment(s) attached is then positioned on the anterior aspect of the proximal ulna and secured in place as described above.

In yet another embodiment, where there is significant compromise of the coronoid process which renders the coronoid fragment irreparable and unable to be surgically repaired, a bone graft is utilized. The bone graft is aligned with the proximal aspect of the plate so as to be adjacent to the threaded holes along the proximal aspect of the plate. Screws are inserted into the threaded holes along the proximal aspect of the bone plate and into the bone graft to secure the bone graft to the bone plate. The screws utilized may be locking or non-locking, self tapping or require that a hole be drilled and tapped. The bone plate with the bone fragment attached is then positioned positioned on the anterior aspect of the proximal ulna and secured in place as described above.

In yet another embodiment, there may be a desire to secure the elbow capsule to the proximal ulna. Typically, this may occur when bone quality is significantly fragmented and poor and there is concern that the elbow capsule will not remain adequately secured to the bone without additional fixation. In one implementation of this, a suture or other flexible device is passed through the elbow capsule leaving several inches of extra length which is then passed through the suture holes arranged along the width of the proximal aspect of the plate. The plate is then placed in position on the anterior aspect of the proximal ulna and the suture or other flexible device is tensioned securing the elbow capsule to the plate.

DETAILED DESCRIPTION OF THE PREFERRED EMBODIMENTS

The present application is directed toward a specifically contoured bone plate and a system and method for ulna fixation. The bone plate, system and method may be used to treat for example, coronoid fractures of the proximal ulna.

Figure 1:
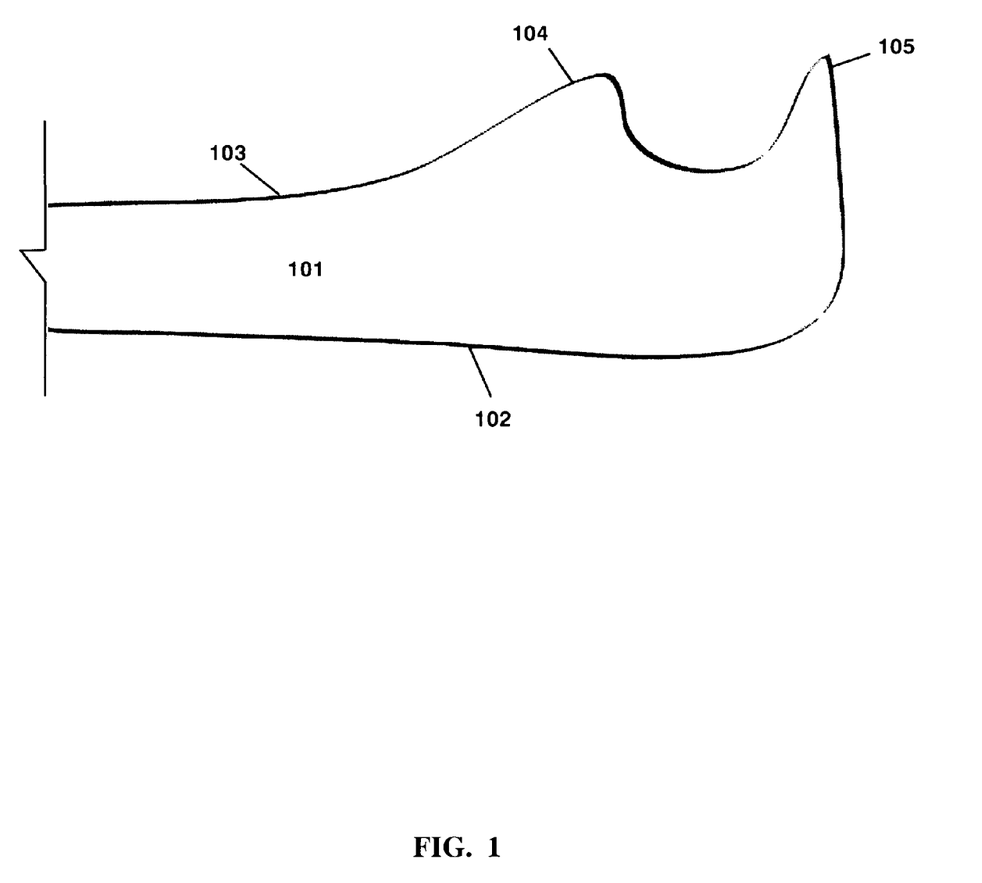
FIG. 1 is a lateral view of the normal anatomy of the proximal ulna.

In general, the bone plate is substantially rigid and specifically contoured to fit the anterior surface of the proximal ulna. The method generally includes securing the bone plate to the anterior surface of the proximal ulna as well as to the coronoid process or a bone graft relative to the fracture. The plate has surfaces that define openings through which screws and/or flexible devices such as suture and cable can pass. The method may also include forming at least one hole through the ulna, passing flexible device through an anchor and then passing the anchor through the hole in the ulna and through the bone plate from posterior to anterior and manipulating the anchor so that it resists passing back through the plate. The suture is then secured to a second anchor on the posterior aspect of the proximal ulna securing the plate in position on the anterior aspect of the proximal ulna. The method may also include inserting at least one bone screw through the ulna from posterior to anterior and into the bone plate. Additionally, the method may include utilizing both flexible device and screws to secure the plate to the bone. Other objects, features, and advantages of the present invention will become more apparent from the following detailed description of the preferred embodiment and certain modifications thereof when taken together with the accompanying drawings in which:

FIG. 1 is a lateral perspective view of the normal anatomy of the proximal ulna 101. The illustration shows the posterior surface 102 of the proximal ulna 101, the anterior surface 103 of the proximal ulna 101, the coronoid process 104 of the proximal ulna 101, and the olecranon process 105 of the proximal ulna 101. As shown in the illustration, the coronoid process 104 of the proximal ulna 101 is located on the anterior surface 103 of the proximal ulna 101.

Figure 2:
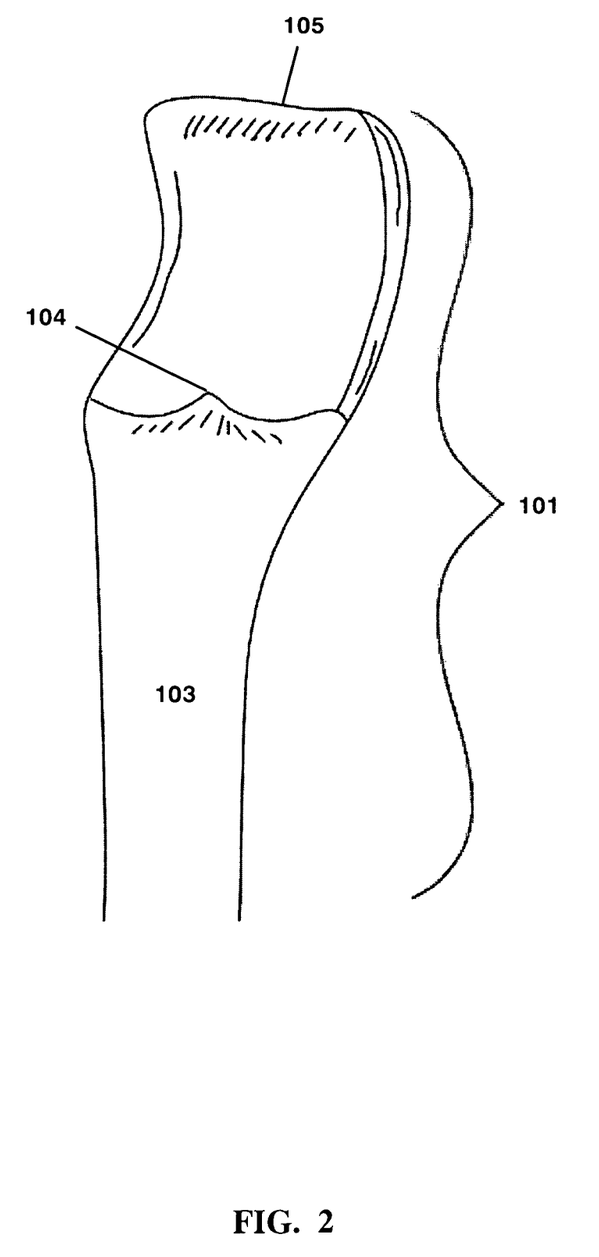
FIG. 2 is an anterior view of the normal anatomy of the proximal ulna.

FIG. 2 is an anterior perspective view of the normal anatomy of the proximal ulna 101. The illustration shows the anterior surface 103 of the proximal ulna 101, the coronoid process 104 of the proximal ulna 101, and the olecranon process 105 of the proximal ulna 101.

Figure 3:
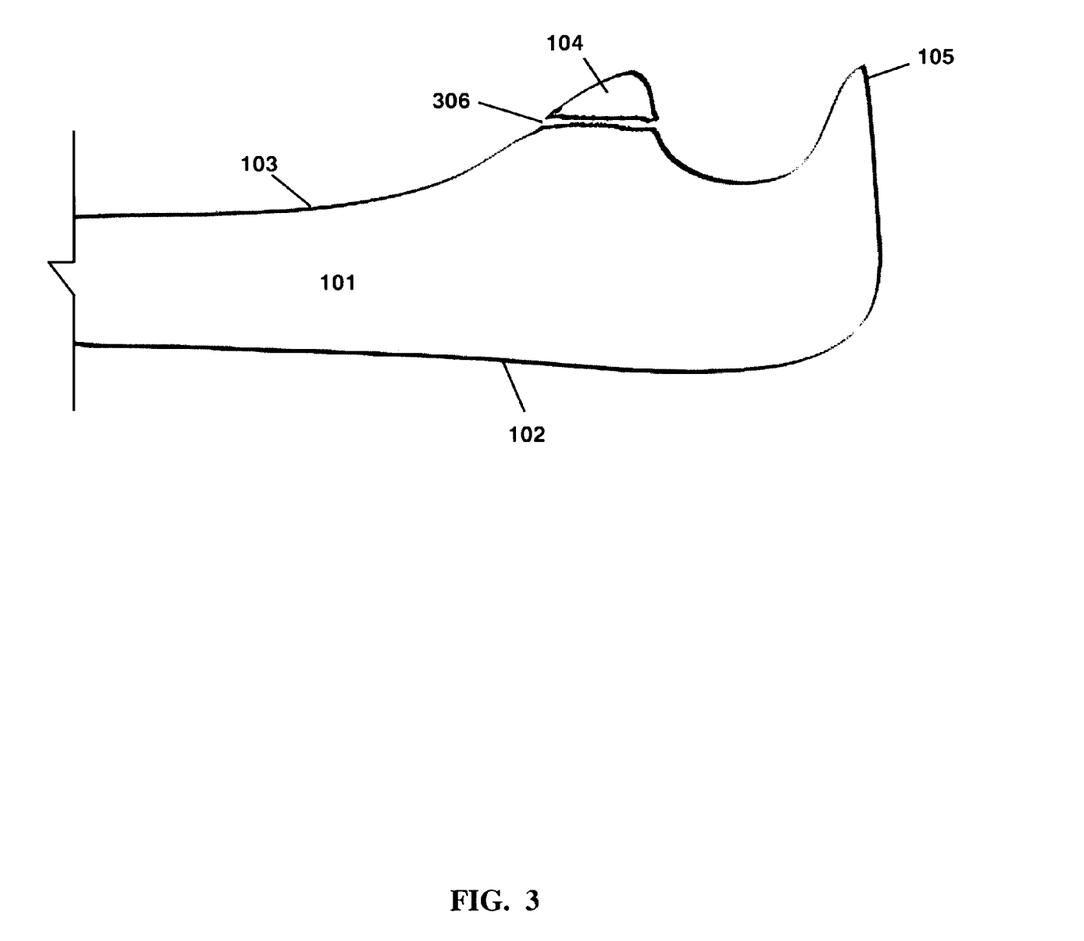
FIG. 3 is a lateral view of the anatomy of the proximal ulna wherein the coronoid process of the proximal ulna has been fractured.

FIG. 3 is another lateral perspective view of the proximal ulna 101 depicting the same structures identified in FIG. 1. The illustration also shows a fracture 306 of the coronoid process 104 of the proximal ulna 101.

Figure 4:
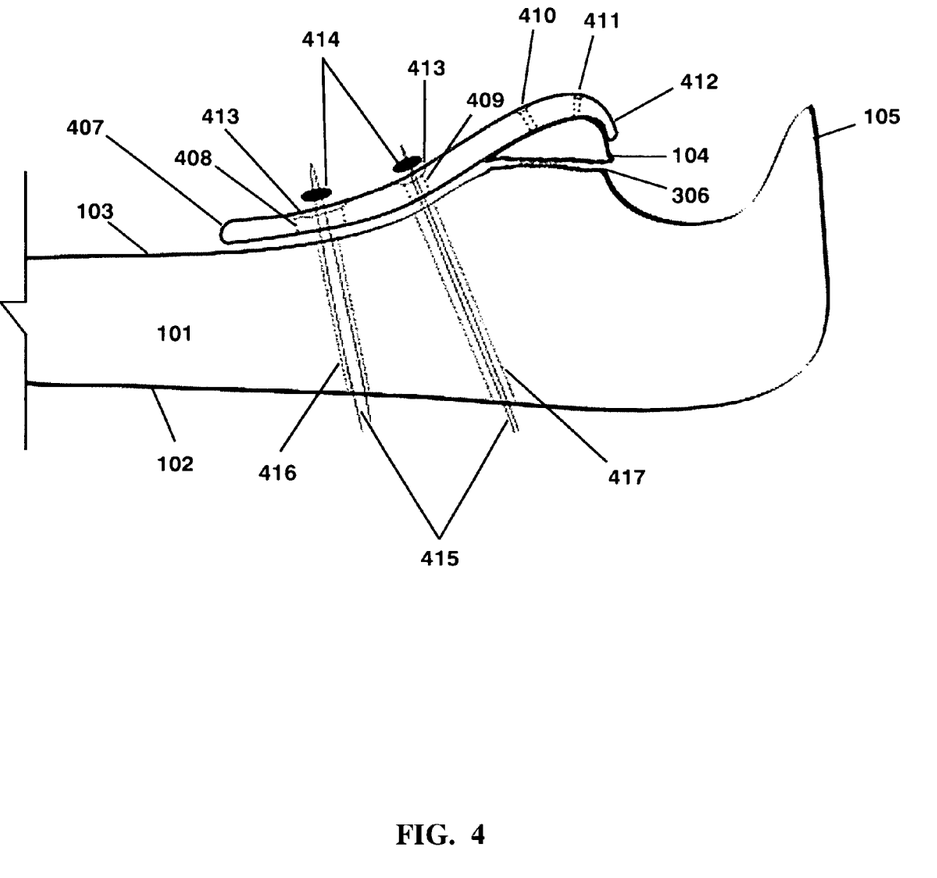
FIG. 4 is a lateral view of the anatomy of the proximal ulna with a fractured coronoid process of the proximal ulna wherein a bone plate has been applied to the proximal ulna with suture and anchors and the suture and anchors are not yet tensioned.

FIG. 4 is a lateral perspective view of the proximal ulna 101 with a fracture 306 of the coronoid process 104 of the proximal ulna 101. The illustration also shows a substantially rigid plate 407 resting on the anterior surface 103 of the proximal ulna 101. The plate 407 is contoured to approximately follow the contours of the anterior aspect 103 of the proximal ulna 101. The illustrated plate 407 has surfaces that define a first opening 408, which is sized so that one or more flexible devices 415 can pass through it, a second opening 409, which is sized so that one or more flexible devices can pass through it, at least one screw hole 410 toward the proximal aspect of the plate 407, which is threaded and sized to permit a screw to pass through it to secure the coronoid fragment 104 or a bone graft (not shown) to the plate 407, and additional smaller holes 411 located at the far proximal aspect of the plate 407, which are sized to permit a flexible device 415 to pass through them and secure the elbow capsule (not shown) to the plate 407. Optionally, as shown, the first opening 408 and the second opening 409 in the plate 407 have a recess 413 at the surface of the plate 407 opposite the anterior aspect 103 of the proximal ulna 101.

The illustration also shows a first hole through the ulna 416, which is drilled utilizing a bone drill (not shown) and is positioned utilizing a low-profile targeting guide (not shown) aligned with the first opening 408 of the plate 407. The flexible device 415 is secured to an anchor 4114 and the anchor 414 with the flexible device 415 attached is passed through the first hole through the ulna 416 and through the first opening 408 in the plate 407. In some embodiments, as shown in the illustration, there is a second hole through the ulna 417, which is drilled utilizing a bone drill (not shown) and is positioned utilizing a low-profile targeting guide (not shown) aligned with the second opening 409 of the plate 407. The flexible device 415 is secured to an anchor 414 and the anchor 414 with the flexible device 415 attached is passed through the first hole through the ulna 416 and through the second opening 409 in the plate 407.

The illustration also shows that the plate 407 possesses a hooked feature 412 at the proximal end of the plate. The hooked feature 412 captures the proximal/anterior aspect of the coronoid process 104 of the proximal ulna 101. The hooked feature 412 has reciprocal mating surfaces to the coronoid process 104 surface that it engages and applies a force in opposition to any potential displacing forces.

Figure 5:
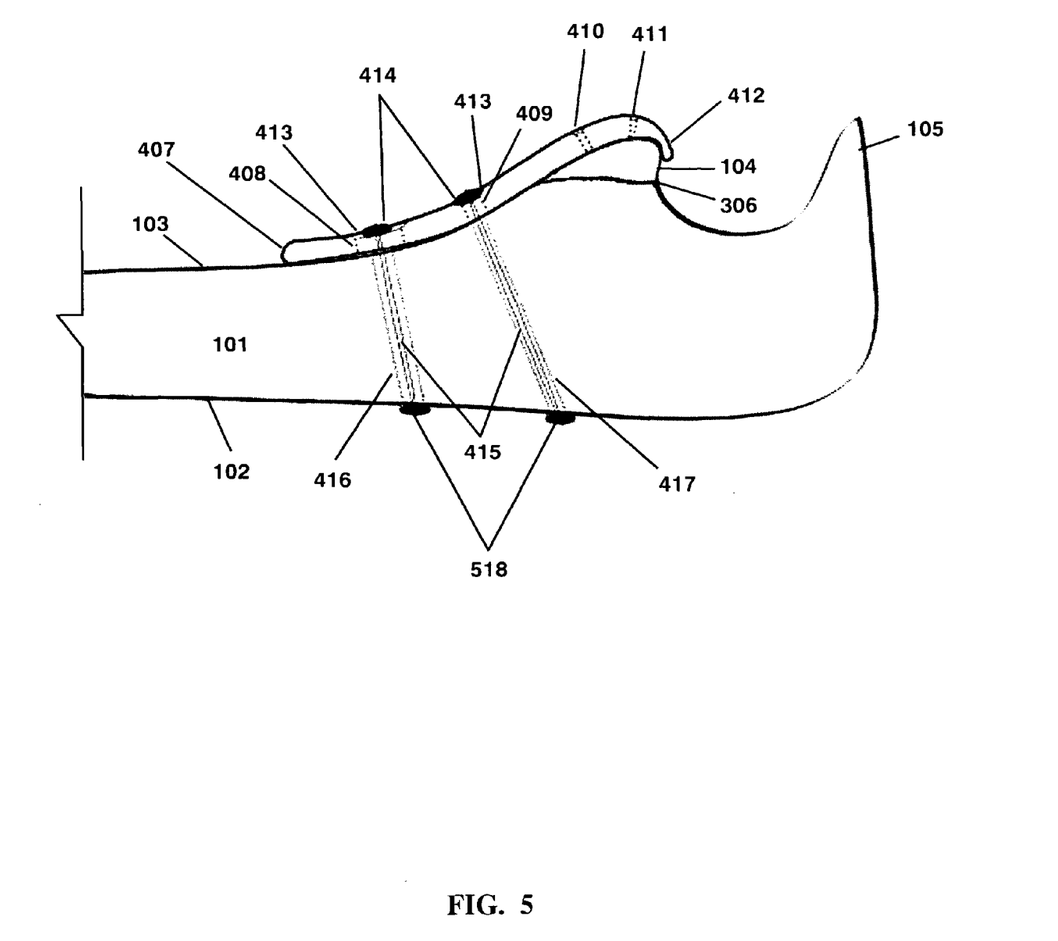
FIG. 5 is a lateral view of the anatomy of the proximal ulna with a fractured coronoid process of the proximal ulna wherein a bone plate has been applied to the proximal ulna with suture and anchors and the suture and anchors have been tensioned thereby affixing the bone plate to the proximal ulna.

In FIG. 5 the anchors 414 are affixed to the plate 407. The anchors 414 are manipulated so as to resist passing back through the first opening 408 and the second opening 409 in the plate 407. An anchor 414 is received into the recess 413 of the first opening 408 in the plate 407 which as shown is elongated and allows the anchor to be adjusted longitudinally within the first opening 408 in the plate 407. An anchor 414 is also received into the recess 413 of the second opening 409 in the plate 407 and fits snugly into the recess 413 of the second opening 409 in the plate 407. The flexible devices 415 attached to the anchors 414 are attached to anchors 518 on the posterior aspect 102 of the proximal ulna 101. The flexible devices 415 are tensioned and secured to the anchors 518 on the posterior aspect 102 of the proximal ulna 101 securing the plate 407 in place on the anterior aspect 103 of the proximal ulna 101.

Figure 6:
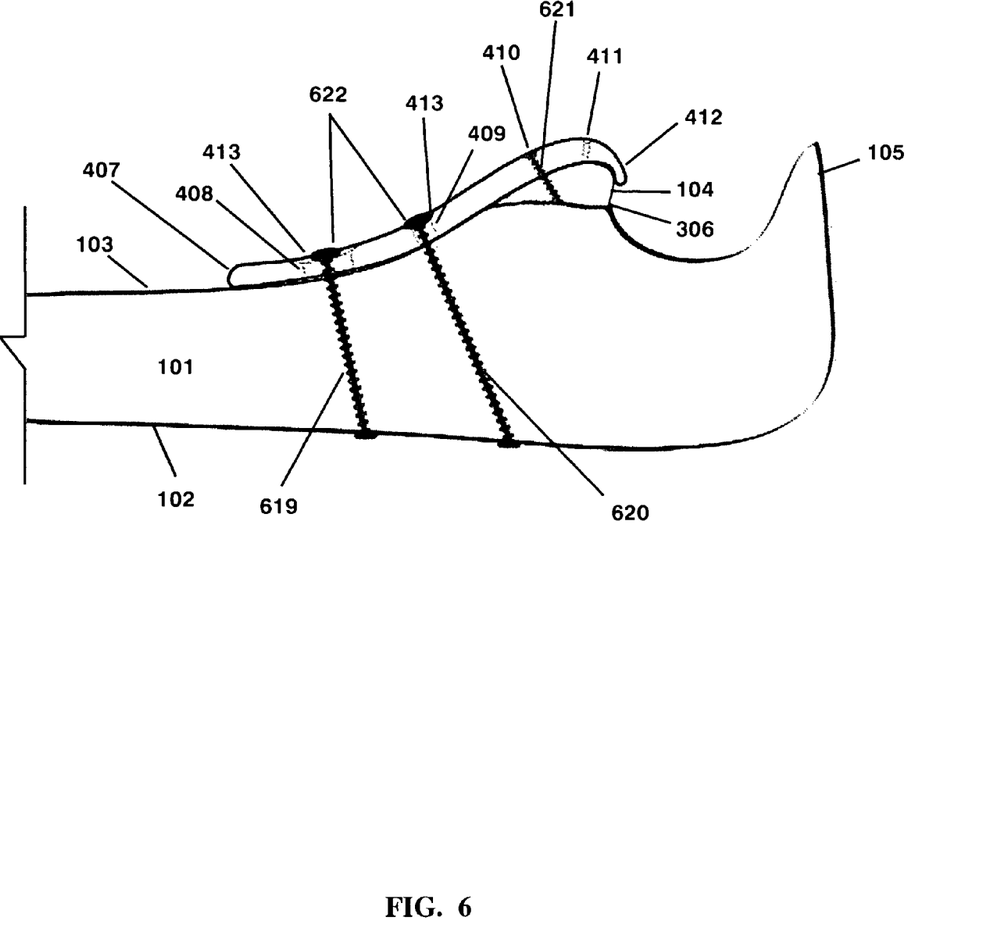
FIG. 6 is a lateral view of the anatomy of the proximal ulna with a fractured coronoid process of the proximal ulna wherein a bone plate has been applied to the proximal ulna with suture and anchors and the suture and anchors have been tensioned thereby affixing the bone plate to the proximal ulna and the fractured coronoid process or a bone graft is secured to the bone plate with screws.

In FIG. 6 the plate 407 is secured to the anterior aspect 103 of the proximal ulna 101 by screws 619 and 620, and the plate 407 is secured to the coronoid fragment 104 or bone graft (not shown) by a screw 621. In the illustration, a low-profile targeting guide (not shown) is aligned with a first opening 408 in the plate and a bone screw 619 is inserted through the proximal ulna 101 from the posterior aspect 102 to the anterior aspect 103 of the proximal ulna and into the first opening 408 in the plate 407. In some embodiments this first opening 408 may be threaded to receive the bone screw 619 and secure the plate 407 to the anterior aspect 103 of the proximal ulna 101. In other embodiments the first opening 408 is not threaded and the bone screw 619 is inserted through the plate 407 and into a threaded device 622 which captures the tip of the screw 619 at a side of the plate 407 opposite the proximal ulna 101.

The illustration also shows, a second bone screw 620 securing the plate 407 to the anterior aspect 103 of the proximal ulna 101. A low-profile targeting guide (not shown) is aligned with a second opening 409 in the plate and a bone screw 620 is inserted through the proximal ulna 101 from the posterior aspect 102 to the anterior aspect 103 of the proximal ulna 101 and into the second opening 409 in the plate 407. In some embodiments this second opening 409 may be threaded to receive the bone screw 620 and secure the plate 407 to the anterior aspect 103 of the proximal ulna 101. In other embodiments the second opening 409 is not threaded and the bone screw 620 is inserted through the plate 407 and into a threaded device 622 which captures the tip of the screw 620 at a side of the plate 407 opposite the proximal ulna 101.

The illustration in FIG. 6 also shows a bone screw 621 securing the coronoid fragment 104 or bone graft (not shown) to the plate 407. The coronoid fragment 104 or bone graft is aligned with the proximal aspect of the plate 407 adjacent to the threaded holes 410 arranged along the width of the proximal aspect of the plate 407. Screw(s) 621 is/are inserted into the threaded holes 410 and through the plate 407 and into the coronoid fragment 104 or bone graft-securing the plate 407 to the coronoid fragment 104 or bone graft.

Figure 7:
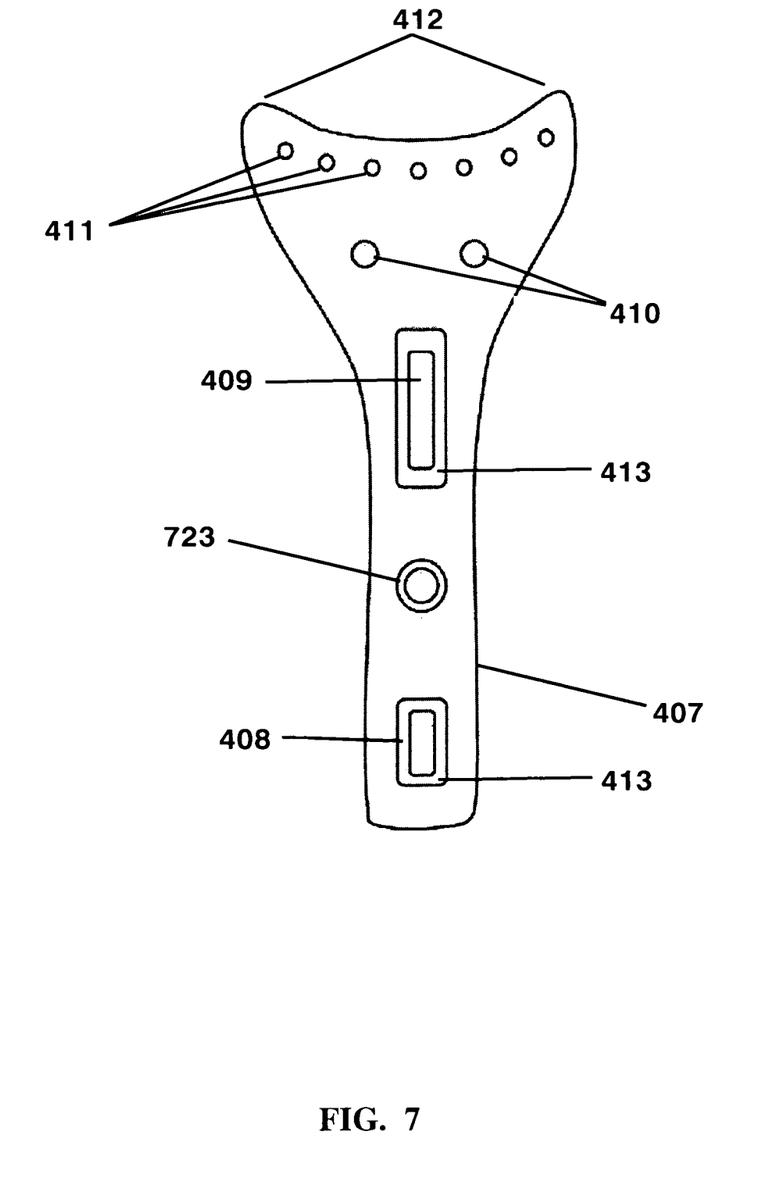
FIG. 7 is an anterior view of the bone plate.

FIG. 7 is an illustration of the anterior aspect of the bone plate 407. The illustration shows a plurality of openings arranged along the length of the plate 407. As shown, these openings may or may not be similar in their shape and dimensions with some having a substantially round appearance such as opening 723, and others having an elongated appearance such as opening 408 and opening 409. As shown, opening 408 and opening 409 possess a recess 413 around the perimeter of the openings. These openings may or may not contain such a recess.

The illustration also shows a plurality of smaller holes 410 arranged along the width of the proximal aspect of the plate. These holes 410 are sized to receive screws 621 to secure the coronoid fragment 104 to the plate 407. At the far proximal aspect of the plate there is a plurality of holes 411 arranged along the width of the proximal end of the plate. These holes 411 are sized to permit flexible device 415 to pass through them to secure the plate 407 to the elbow capsule (not shown). In one embodiment a flexible device 415, such as suture or cable, is passed through the elbow capsule and then passed through the plate 407, and when the plate 407 is placed in position on the anterior aspect 103 of the proximal ulna 101 the suture is tensioned securing the plate to the elbow capsule.

A number of embodiments have been described. Nevertheless, it will be understood that various modifications may be made without departing from the spirit of the scope of the invention. For example, the physical shapes and dimensions of the various system components, (e.g. the plate, the anchors, the screws, and the flexible device) can vary considerably.

For example, in some implementations, the anchor may be a washer that is elongated and the recess in the plate in which the anchor fits, may also be elongated. In such an implementation, there may be row of holes in the washer that extends along the length of the elongated washer. The washer can have any number of holes. Typically, the holes are formed in line with one another, however, they need not be aligned with one another.

The suture can pass through any two adjacent or non-adjacent holes in the washer and be tied above the washer. Typically, the specific holes that the suture passes through may be selected so that when the suture is tied and tightened above the washer, the plate is most effectively reduced to the bone.

The number and arrangement of screws used to secure the plate to the coronoid fragment or bone graft can be changed. Indeed, any number of screws may be used and the screws may be arranged in a variety of ways. The screws can be self-tapping or require that a hole be drilled and tapped. Moreover, other methods of securing the plate to the coronoid fragment or bone graft may be used, such as the use of adhesives.

In some implementations, the proximal end of the plate is flared medially, laterally, or both to accommodate, for example, side-by-side screw hole placement. In some implementations, the plate does not include a recess for receiving the anchor. In those instances, when installed, the anchor may simply be positioned above the plate, but not in a recess. In some implementations, the recess is slightly larger than the anchor to allow its position relative to the plate to be adjusted.

In a plate that includes holes for securing a suture or other flexible device, the holes may or may not be evenly spaced. The holes may or may not extend along substantially the entire width of the proximal aspect of the plate and there may or may not be a second row of holes running parallel to the first row of holes along the width of the proximal aspect of the plate. In some implementations, the holes arranged along the length of the plate can be offset from the fixation plate's longitudinal centerline. In some implementations, only one row of holes may be provided, while in others there may be more than one row.

A variety of different plates may be used in connection with the foregoing techniques. Typically, the plates would be contoured to accommodate common anatomic variants of proximal ulnas. In some implementations, the plate may have some degree of malleability.

The steps of the techniques described can be performed in a variety of different orders. In some instances, one or more of the steps described herein may be discarded completely.

Other implementations are within the scope of the claims.

What is claimed is:

1. A substantially rigid bone plate, comprising:
 a contoured upper surface;
 a lower surface configured for application to a coronoid process of a proximal ulna;
 a hooked feature on a proximal aspect of the plate configured to capture the most proximal/anterior aspect of the coronoid process and to apply a force in opposition to displacing forces;
 a plurality of holes arranged along a length of the plate configured to accommodate means to secure the plate to the ulna;
 a plurality of threaded holes arranged along a width of the proximal end of the plate configured to accommodate means to secure the plate to a coronoid fragment or a bone graft; and
 a plurality of smaller holes arranged along the width of the proximal end of the plate configured to accommodate suture or other flexible device fixation of the anterior elbow capsule.

2. The bone plate of claim 1 further comprising means to secure the plate to the ulna and means to secure the plate to the coronoid fragment or the bone graft, wherein the means to secure the plate are a plurality of flexible devices.

3. The bone plate of claim 2 wherein the flexible devices are suture.

4. The bone plate of claim 2 wherein the flexible devices are cable.

5. The bone plate of claim 2 wherein the flexible devices are a combination of suture, cable and other flexible devices.

6. The bone plate of claim 1 further comprising means to secure the plate to the ulna and the means to secure the late to the coronoid fragment or the bone graft, wherein the means to secure the plate are a plurality of bone screws.

7. The bone plate of claim 1 further comprising means to secure the plate to the ulna and the means to secure the plate to the coronoid fragment or the bone graft, wherein the means to secure the plate are a combination of flexible devices and bone screws.

8. The bone plate of claim 6 wherein the bone screws are locking screws.

9. The bone plate of claim 6 wherein the bone screws are non-locking screws.

10. The bone plate of claim 6 wherein the bone screws are self tapping.

11. The bone plate of claim 6 wherein the bone screws are non-self tapping.

12. The bone plate of claim 1 wherein the plurality of holes arranged along the length of the plate are elongated holes.

13. The bone plate of claim 1 wherein the plurality of holes arranged along the length of the plate are round holes.

14. The bone plate of claim 13 wherein the plurality of holes arranged along the length of the plate are threaded holes.

15. The bone plate of claim 13 wherein the plurality of holes arranged along the length of the plate are a combination of threaded and non-threaded holes.

16. The bone plate of claim 1 wherein the plurality of holes arranged along the length of the plate are a combination of round and elongated holes.

17. The bone plate of claim 1 wherein the plate flares out medially as it approaches the proximal extent and hooked feature.

18. The bone plate of claim 1 wherein the plate flares out laterally as it approaches the proximal extent and hooked feature.

19. The bone plate of claim 1 wherein the plate flares out both medially and laterally as it approaches the proximal extent and hooked feature.

20. A method of ulna fixation for treating a fractured coronoid process of the proximal ulna, the method comprising:
 securing a substantially rigid plate with hooked features on its proximal aspect to the anterior aspect of the proximal ulna so that it extends proximally to capture the anterior aspect of the coronoid process of the proximal ulna with the hooked features, wherein the hooked features are configured to apply a force to the coronoid process in opposition to displacing forces;
 aligning a low-profile targeting guide with the first opening in the plate;
 forming a hole through the ulna connecting the posterior to anterior aspects of the proximal ulna;
 securing a flexible device to a first anchor;
 passing the first anchor with flexible device attached through a hole through the ulna from posterior to anterior, and a hole in the anteriorly placed plate;
 manipulating the first anchor so that it resists passing back through the plate;
 positioning a second anchor, coupled to the flexible device, on the posterior aspect of the ulna; and
 tensioning the flexible device.

21. The method of claim 20, further comprising:
 aligning a low-profile targeting guide with a second opening in the plate;
 forming a second hole through the ulna connecting the posterior to anterior aspects of the proximal ulna;
 securing a second flexible device to a third anchor;
 passing the third anchor with flexible device attached through the second hole through the ulna from posterior to anterior, and a second hole in the anteriorly placed plate;
 manipulating the third anchor so that it resists passing back through the plate;
 positioning a fourth anchor, coupled to the second flexible device, on the posterior aspect of the ulna; and
 tensioning the second flexible device.

22. The method of claim 20, wherein the first anchor has a flexible device pre-secured to it.

23. The method of claim 21, wherein the third anchor has a flexible device pre-secured to it.

24. The method of claim 20, further comprising:
securing the plate to the coronoid fragment or bone graft by aligning the coronoid fragment or bone graft with the proximal aspect of the plate so as to be adjacent to the plurality of threaded holes arranged along the width of the proximal aspect of the plate; and
securing the coronoid fragment or bone graft to the proximal aspect of the plate by inserting screws through the plate and into the coronoid fragment or bone graft.

25. The method of claim 21, further comprising:
securing the plate to the coronoid fragment or bone graft by aligning the coronoid fragment or bone graft with the proximal aspect of the plate so as to be adjacent to the plurality of threaded holes arranged along the width of the proximal aspect of the plate; and
securing the coronoid fragment or bone graft to the proximal aspect of the plate by inserting screws through the plate and into the coronoid fragment of bone graft.

26. The method of claim 20, further comprising:
securing the elbow capsule to the plate by passing a length of flexible device through the elbow capsule, leaving several inches of extra flexible device length;
passing the extra flexible device length through the holes arranged along the width of the proximal aspect of the plate; and
positioning the plate on the anterior aspect of the proximal ulna; tensioning the flexible device securing the elbow capsule to the plate.

27. The method of claim 21, further comprising:
securing the elbow capsule to the plate by passing a length of flexible device through the elbow capsule, leaving several inches of extra flexible device length;
passing the extra flexible device length through the holes arranged along the width of the proximal aspect of the plate;
positioning the plate on the anterior aspect of the proximal ulna; and
tensioning the flexible device securing the elbow capsule to the plate.

28. The method of claim 20, wherein a first opening in the plate is elongated in a direction that generally follows the length of the ulna, and wherein a first hole through the ulna is aligned with at least part of the first opening in the plate.

29. The method of claim 20, wherein a first opening in the plate contains a recess at a side thereof opposite the ulna, and wherein the recess is adapted to receive the anchor, the method further comprising positioning the anchor substantially within the recess and engaging the flexible device to the anchor.

30. The method of claim 29, wherein the anchor is adapted to fit snugly into the recess.

31. The method of claim 21, wherein a second opening in the plate contains a recess at a side thereof opposite the ulna, and wherein the recess is adapted to receive the anchor, the method further comprising positioning the anchor substantially within the recess and engaging the flexible device to the anchor.

32. The method of claim 31 wherein the anchor is adapted to fit snugly into the recess.

33. The method of claim 20, wherein the anchor is substantially oblong and has one or more surfaces that define one or more holes distributed longitudinally across the anchor.

34. The method of claim 20, wherein the first opening is threaded to receive a screw, and said method further comprising:
aligning a low-profile targeting guide with the first opening;
inserting a bone screw through the ulna, from posterior to anterior, and through the first opening in the plate where the threads of the bone screw are captured by the threads of the first opening.

35. The method of claim 20, wherein the first opening is not threaded, and said method further comprising:
aligning a low-profile targeting guide with the first opening;
inserting a bone screw through the ulna, from posterior to anterior, through the first opening and into a threaded washer or other capturing device positioned on a side of the plate opposite the anterior aspect of the proximal ulna.

36. The method of claim 21, wherein the second opening is threaded to receive a screw, and said method further comprising:
aligning a low-profile targeting guide with the second opening;
inserting a bone screw through the ulna, from posterior to anterior, and through the second opening in the plate where the threads of the bone screw are captured by the threads of the second opening.

37. The method of claim 21, wherein the second opening is not threaded, and said method further comprising:
aligning a low-profile targeting guide with the second opening;
inserting a bone screw through the ulna, from posterior to anterior, through the second opening and into a threaded washer or other capturing device positioned on a side of the plate opposite the anterior aspect of the proximal ulna.

38. A fixation system for a fracture of the proximal ulna, the fixation system comprising:
a substantially rigid plate with hooked features on a proximal aspect configured to be secured to an anterior aspect of the proximal ulna relative to the fracture, wherein the secured plate is configured to extend over the coronoid process with the hooked features configured to capture the most proximal/anterior aspect of coronoid process and to apply a force in opposition to any displacing forces, the plate having one or more surfaces that define a plurality of openings through which a flexible device or screw can pass;
an anchor configured to be positioned at a side of the plate opposite the proximal ulna and adjacent to a first opening;
a suture secured to an anchor and configured to extend through a first opening in the plate, through a hole in the proximal ulna and secured to an anchor for positioning on the posterior surface of the proximal ulna.

39. The fixation system of claim 38 wherein the first opening is elongated and extends in a longitudinal direction along the plate.

40. The fixation system of claim 38 wherein the first opening is round.

41. The fixation system of claim 38 wherein the first opening in the plate defines a recess adapted to receive the anchor at a side of the plate opposite the ulna.

42. The fixation system of claim 41 wherein the anchor fits substantially snugly in the recess.

43. The fixation system of claim 38, wherein the anchor has a hole or holes dimensioned to receive flexible device.

44. The fixation system of claim 38, wherein the anchor is oblong and dimensioned to pass through the hole in the ulna and through the hole in the plate, and dimensioned to resist passing back through the plate once positioned on the anterior aspect of the plate.

45. The fixation system of claim 38, further comprising a plurality of openings at the proximal aspect of the plate, wherein the plurality of openings are configured to receive a screw to secure the coronoid fragment or bone graft to the plate.

46. The fixation system of claim 38, wherein at least one of a plurality of openings arranged along the length of the plate is threaded to receive a screw.

47. The fixation system of claim 38, wherein at least one of a plurality of openings arranged along the length of the plate is not threaded.

48. A proximal ulna fixation kit comprising:
  a substantially rigid, specifically contoured plate configured to be secured to the anterior aspect of the proximal ulna;
  hooked features at a proximal aspect of the plate configured to capture the most proximal/anterior aspect of the coronoid process of the proximal ulna and to apply a force in opposition to any displacing forces,
  the plate having surfaces that define:
    a plurality of openings arranged along the length of the plate through which a flexible device and anchor or screws can pass; and
    a plurality of holes arranged along the width of the proximal end of the plate through which a flexible device can pass; and
    a plurality of holes arranged along the width of the proximal end of the plate through which screws can pass;
  a plurality of fastening devices configured to pass through an opening in the plate to secure the plate to the anterior aspect of the proximal ulna;
  a plurality of anchors can be positioned configured for positioning at a side of the plate opposite the ulna;
  a plurality of anchors configured for positioning on the posterior aspect of the proximal ulna;
  a plurality of flexible devices configured for joining an anchor configured to be positioned at a side of the plate opposite the ulna and an anchor configured to be positioned on the posterior aspect of the proximal ulna;
  a plurality of screws configured to pass through any of the second row of holes arranged along the width of the proximal end of the plate;
  a plurality of screws configured for insertion through the ulna, from posterior to anterior, and for securing to the plate on the anterior aspect of the ulna;
  a plurality of flexible devices configured to pass through any of the first row of holes for securing the elbow capsule to the plate.

* * * * *